United States Patent [19]

Markham

[11] Patent Number: 5,141,581
[45] Date of Patent: Aug. 25, 1992

[54] IMPLANTS WITH A COVER WHICH RESISTS FORMATION OF FIRM SPHERICAL ENCAPSULATION

[76] Inventor: Harold A. Markham, 6637 Drexel Ave., Los Angeles, Calif. 90048

[21] Appl. No.: 391,731

[22] Filed: Aug. 8, 1991

Related U.S. Application Data

[63] Continuation of Ser. No. 170,641, Mar. 16, 1988, abandoned, which is a continuation of Ser. No. 718,813, Mar. 20, 1985, abandoned, which is a continuation-in-part of Ser. No. 668,691, Nov. 6, 1984, abandoned, which is a continuation of Ser. No. 433,399, Oct. 8, 1972, abandoned.

[51] Int. Cl.⁵ .............................................. B32B 31/18
[52] U.S. Cl. ..................... 156/242; 156/245; 264/46.4; 264/259; 264/260; 623/7; 623/8; 623/11
[58] Field of Search ............... 156/242, 245; 264/46.4, 264/259, 260; 623/7, 8, 11

[56] References Cited

U.S. PATENT DOCUMENTS

| | | |
|---|---|---|
| 2,665,520 | 5/1972 | Perras et al. |
| 2,842,775 | 7/1958 | Pangman |
| 3,189,921 | 6/1965 | Pangman |
| 3,293,663 | 12/1966 | Cronin ................................. 623/8 |
| 3,366,975 | 2/1968 | Pangman ............................. 623/8 |
| 3,559,214 | 2/1971 | Pangman ............................. 623/8 |
| 3,683,424 | 8/1972 | Pangman ............................. 623/8 |
| 3,852,832 | 12/1974 | McGhan et al. ..................... 623/8 |
| 3,852,833 | 12/1974 | Koneke et al. ...................... 623/8 |
| 3,879,245 | 4/1975 | Fetherston et al. ............... 156/245 |
| 4,249,975 | 2/1981 | Rechenberg ...................... 156/245 |
| 4,307,472 | 12/1981 | Morris ............................... 623/11 |
| 4,608,052 | 8/1986 | Kampen et al. .................... 623/18 |

FOREIGN PATENT DOCUMENTS

| | | | |
|---|---|---|---|
| 2821354 | 11/1978 | Fed. Rep. of Germany | ........ 623/16 |
| 2827077 | 1/1980 | Fed. Rep. of Germany | . |
| 1506271 | 10/1965 | France | . |

Primary Examiner—Caleb Weston
Attorney, Agent, or Firm—Vorye, Sater, Seymour and Pease

[57] ABSTRACT

A transition layer for an implant to be placed in the human body. The implant has a core, and the transition surface surrounds the core. The transition layer is an open celled foam with cut surfaces. An adhesive adheres one surface to the core, and penetrates the transition layer a limited distance so as to leave over the entire surface, microstructures of cell fragments providing for tissue attachment without formation of a firm encapsulation.

19 Claims, 2 Drawing Sheets

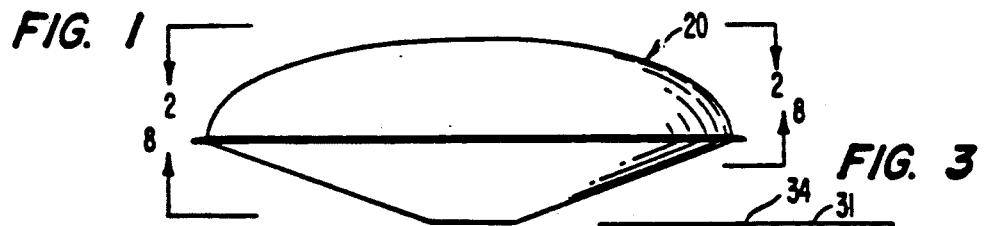
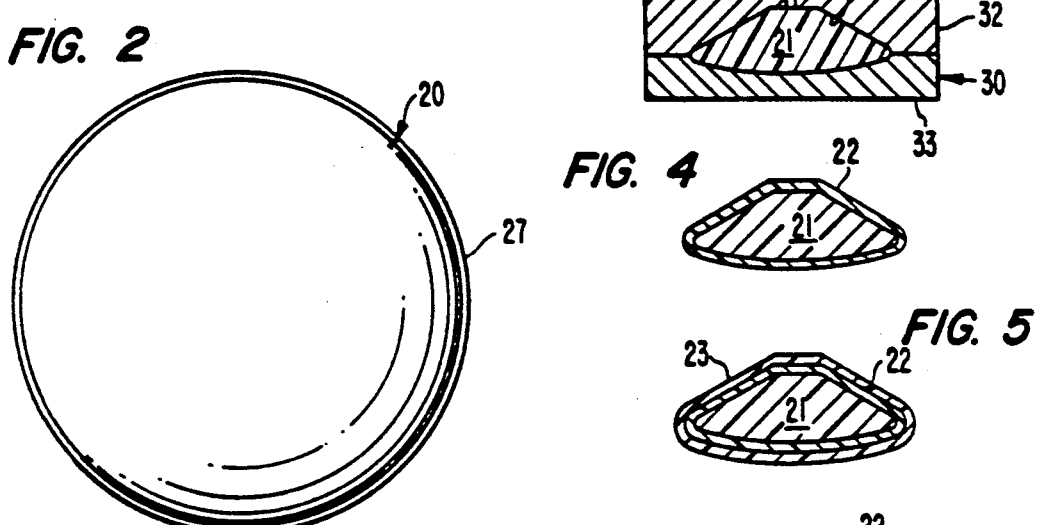
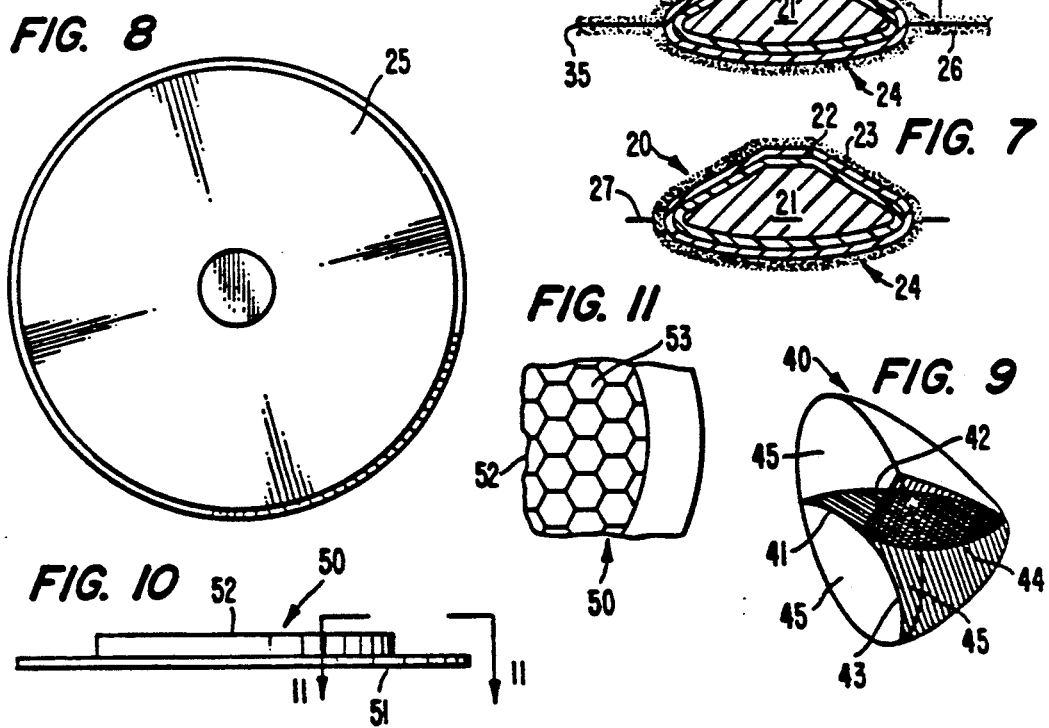

IMPLANTS WITH A COVER WHICH RESISTS FORMATION OF FIRM SPHERICAL ENCAPSULATION

This application is a continuation of Ser. No. 170,641, filed mar. 16, 1988, abandoned, which is a continuation of Ser. No. 718,813, filed Mar. 20, 1985, abandoned, which is a continuation-in-part of Ser. No. 668,691, filed Nov. 6, 1984, abandoned, which is a continuation of Ser. No. 433,399, filed Oct. 8, 1982, abandoned.

Field of the Invention

This invention relates to implants for implantation in the human body which resist the formation of firm spherical encapsulation.

Background of the Invention

Implants are widely used in the human body to substitute for missing tissue or structure, thereby emulating more natural, or ccreating more pleasing, external body contours. An example is the mammary prosthesis, which is used for cosmetic augmentation, and for tissue replacement in reconstructive procedures. Other shapes exist to augment or replace other tissues or types of tissues, for example testicular prostheses to simulate a missing testicle. Other types of devices are implanted, often for a medical or a physiological objective, rather than, for cosmetic advantage. One such implant is the pacemaker, which is a device which is subcutaneously implanted at the sternum, and which delivers electrical currents to a heart which does not reliably generate its own currents. Newer variants of such devices sense fibrillation in the heart, and deliver corrective currents. Still other examples are porous bodies which contain pharmaceuticals to be released gradually into the body.

The selection of materials from which such implants can be made is very limited, because the material when in contact with tissue must be tissue-compatible to avoid rejection, must not be carcinogenic, and for mammary implantation, its body must have physical properties such as density, deformability in the sense of pliability, shape, memory, and the like, that enable it reasonably to simulate the tissue which otherwise would normally would be there.

The foregoing objectives when first contemplated appear to be readily attainable, and to the extent they have been described, they are. However, a prosthesis does not merely reside in its region of implantation as an independent entity. Instead, the surrounding tissues have their own properties. These properties are not only their inherent ones of normal pliability and the like, but also those which relate to their interaction with foreign bodies that are implanted in them. At this point the matter becomes very much more complicated, because surrounding tissues and fluids have their own interactive properties, and these can cause abrupt interface conditions that can result in hard spherical encapsulations or in poor fixation. Hard encapsulations are scarcely to be desired around a mammary prosthesis, because the illusion of original tissue is entirely lost. Neither is a "floating" situation, where the prosthesis becomes in effect a palpable and separately noticeable and uncomfortable structure lacking adjoining tissue congruity just beneath the skin. There is supposed to be only one detectable tissue body in each breast, for example, and a loose prosthesis is detected as a separate body.

Still another problem can result from excessive penetration of surrounding tissues and fluids into the prosthesis. Then the prosthesis as a gross body takes on different properties to a greater depth than that of a mere encapsulation. Again, the undesirable result is a palpably distinguishable and often quite firm or even hard structure.

Soft tissue replacement or augmentation prostheses are not the only types which are affected by this tissue reaction There are many types of quite rigid implants, for example pacemakers, which can be felt without cosmetic dismay, but which when encapsulated by a firm encapsulation become very uncomfortable to the user. The perceived effect is one of a constriction of the tissue around the body, which is very uncomfortable.

Thus, prosthesis design involves severals sets of problems. The easiest to attend to is the approximation of gross properties, such as palpability, specific gravity, total weight, suitable shapes, and the like, when these are appropriate. This is because these gross properties can readily be achieved by suitable modification of readily available materials. But at the interface or transition surface, where the implanted body interacts with the surrounding tissues and fluids, the problem becomes much more complicated, and unless the problem is fully solved, there is a high risk of formation of a too, firm or even a hard encapsulation which ultimately may require surgical intervention.

This invention is not the first attempt to meet the stated objectives, and indeed there have been some innovative and resourceful efforts made to meet them. Still, until this invention was made, some ultimate properties and the suitability of previous prostheses were often unpredictable, or undesirable, or both, and the user was frequently subjected to discomfort, inconvenience, and embarrassment. It should be recognized at this point that in the instant invention a capsule is indeed formed. However, it is a soft and sponge-like capsule which is not separately palpable, and a good fixation is still attained.

Additional problems arise as the consequence of the gross properties of a material. Often enough a gross prothesis made entirely from one material will not function effectively. For this reason there exists the well-known practice of making prostheses from a plurality of materials - one for the inner mass of the prosthesis, and another for the external wall or surface. The purpose in soft tissue replacement or augmentation is to provide the most biologically and structurally compatible properties for the external interface between the prosthesis and the contiguous tissue, thereby acting as a delivery system so that the implant's "filling" can achieve the gross tissue-emulating objectives. The raw filling material could not have made a suitable interface Such prostheses involve the additional requisite that, even though the filling such as a gel or liquid is usually contained in an envelope of some kind, the contained material still must not be harmful to the patient in case the envelope is violated such as by being pierced, or if it somehow leaks, or is otherwise permeable. Other types of prostheses, for example pacemakers, are their own "filling", i.e., a rigid case. They are not expected to leak, but neither is it desirable for firm spherical encapsulation to grow around them. It is even possible for the body to expel any type of encapsulated prosthesis through the skin, much as a piece of shrapnel is expelled if a hard encapsulation is formed. The course of such an event is troubling and uncomfortable, and calls for surgical intervention which it is best to avoid if possible.

Implantable prostheses (other than metallic prostheses), especially mammary prostheses, have had an interesting and relatively brief career, in part because tissue-compatible materials such as medical grade silicone elastomer and medical grade polyurethane are themselves of relatively recent origin. Earlier prostheses tended to utilize a total core or block of a sponge-like foam material, because of all of the then available useful materials, its physical properties were closest to those of tissue cells. Also, any desired shape could readily be carved from a block of such material. An example of such a prosthesis is shown in Pangman Pat. No. 2,842,775. Such prostheses often, even usually, suffered from an undesirable hard encapsulation which developed after implantation, not only from tissue reactions at and just beneath the interface with the tissue, but also from deep penetration of collagen fibers into the foam. These led to undesirable hardness and the product was generally regarded as much less than optimum. Nevertheless, these prostheses were extensively used for a long time, because they were the best available, but their inherent shortcomings naturally led to further improvements.

Whatever the "core" of a prosthesis is such as, a silicone body, silicone sac filled with fluid or gel, gel body with a sealed surface, or a plastic or metal case, the core should be able to be made proof against leakage of fluid into it or out of it unless leakage out of it is desired, as will later be disclosed. Although this invention relates primarily to soft tissue prostheses, and the principal embodiments refer to that use, the principal thrust of this invention is not to the core itself, but to its covering, which is the interface with tissues and fluids, and which is intended to resist the formation of firm spherical encapsulations, and thereby to make any kind of implant more acceptable to the human body, still attaining a good fixation. In fact, the covering for the core can even be loose from it, such being provided as a sac or a sleeve, in which the core is placed, the sac carrying the interface material on its surface.

As to the problem of fixation or connection at the implantation site, it is highly undesirable in many applications, for example in mammary prostheses, for there to be any relative shear motion between the prosthesis and the surrounding tissue. This would result in a movable, rather than a pliable, prosthesis, and reflect a failure to incorporate the prosthesis into the tissue system. Attempts have been made to provide porous surfaces into which tissue could grow to prevent segregation of the surface structure of the prosthesis from the surrounding tissue. Such efforts have customarily involved the use of various kinds of foam layers, both open cell and closed cell. These layers, in turn, have created problems of their own. For example, because of the combined porosity and thickness of the layers, the tissue often tended either to migrate into it to fill the layer, or to create a heavy surrounding layer of firm fibrous tissue. Both of these results are highly undesirable, because in one case the gross properties of the foam are undesirably altered, and in the other, the foam becomes encapsulated by a structure which obscures the gross properties, or prevents them from being utilized, and adds a texture or rigidity of its own.

By now it is generally agreed that to achieve fixation and structural congruity to a foreign body, tissue needs a means of "recognition" so as to "be satisfied" that necessary regrowth is attained and that healing is in close approximation to the normal cellular environment. Attempts have been made in the implant art to utilize woven fabrics such as velours, and foam or sponge covers to function as an outer layer for a prosthesis for the purpose of providing a controlled environment into which tissue can grow and then stop growing. However, in general such materials as utilized have not improved much over the results of smooth surfaces which provide no structural terminal for the connecting cells and all too frequently are encapsulated by a firm or hard capsule. This apparently is because their denseness encourages too much growth, which leads to excessive firmness. Some roughness of the surface of the layer is believed to be necessary, but not an excessive degree of roughness or density. Also, excessive porosity has led to undesirable results. Furthermore, it appears that prostheses made utilizing the prior knowledge of the art probably have surface properties which vary from area to area over the total surface of the prosthesis.

Stated another way, previously no one has really known exactly how to make the structure uniformly and correctly over its entire surface. Besides, there was insufficient knowledge about what was "right". This compounded the difficulty of manufacturing suitable and uniform products, especially if the "model" is simply one that "worked" without an awareness of what aspect it was that was successful and which made it work.

It appears that tissue reacts unfavorably to smooth surfaces in the path of regrowth. The efforts to provide fixation by means of tissue in growth by providing roughened or porous surfaces for in growth have fortuitously also tended to improve the tissue regeneration itself. However, this has been a fortuitous matter, and prior to the instant invention, the invention does not believe there was a total or even a sufficient awareness of the problems to be solved, and certainly there was not a solution developed in which a prosthesis could reliably be manufactured in production processes with uniform desirable surface properties.

At last the inventor has, to his satisfaction, and to the satisfaction of extensive scientific and clinical trials, developed a prosthesis (implant) which has uniformly from component-to-component and uniformly over the entire critical surface of the prosthesis, been successfully functional. In so doing, the objective has been to provide a prosthesis which can be surfaced with a layer of material that provides substantial intercellular continuity without hard spherical encapsulation and contracture.

It is another objective of this invention to enable other types of prostheses to successfully be used - for example, even previously undesirable envelope types, such as metal and plastic cases, or smooth surfaced bodies, by providing a cover for them which isolates from the surrounding tissue the parts of the prosthesis which would give rise to complications from the tissue, while also still providing means for tissue-to-material connection and fixation.

An example of the closest prior art, which reflects many of the above problems, and in which the instant inventor participated, is described in "*Further Studies on the Natural-Y Breast Prosthesis*", Vol. 49, No. 4, copyright 1972. In this article, there is described an earlier prosthesis with a silicone bag that is filled with some suitable substance. Then a newer, more pertinent prosthesis is described which has a silicone sheath filled with a soft, viscous silicone gel that is covered by a one millimeter thick layer of "fine-cell" polyurethane. A "Natural-Y" web is disposed inside the sheath (envelope). The prosthesis described in this article did produce a substantial improvement over its prior art, but also it had problems of its own, such as producibility of a uniform product, not only from prosthesis-to-prosthesis, but from area-to-area of the individual prosthesis. Part of this problem seems to have arisen from a latent uncertainty about precisely what the problems were, and to the extent they were understood, how to make a correct product, especially in quantity production.

Here it is fair to call attention to the fact that while prostheses have been made commercially in very substantial numbers, their manufacture is still very labor-intensive, and calls for considerable dexterity and skill by the person who makes it. It is not unusual for an individual mammary prosthesis to be in the course of manufacture for several working days. Furthermore, there is a near-artistry involved in applying some layers just exactly as they should should be, which even highly skilled artists and highly skilled manufacturing personnel find difficult to learn. Although this invention does require considerable skill in manufacture, still it has proven to be economically manufacturable in high-grade clean room operations.

BRIEF DESCRIPTION OF THE INVENTION

This invention is used for implantation of a core, which core comprises a bulk in the sense of having a volume which occupies space and has an outer surface (sometimes called a boundary layer) which is unsuitable for an interface with surrounding tissues and fluids. In a pacemaker or other rigid articles, for example, this would be the smooth surface of its case. In a prosthetic type of implant, representing the presently preferred application of the invention, the core provides various gross properties such as pliability, specific gravity, and the like which will be desired for the prosthesis as a unit. Upon this boundary layer there is attached a transition layer having as its outermost surface a tissue-receptive region. When this invention is provided as a sac or a sleeve, the sac or sleeve will include a layer which is defined as the boundary layer that will abut and surround the remainder of the core.

The tissue-receptive region of the transition layer provides a volume of fine microfiber-like structures as the outer surface of the prosthesis around which tissue will grow, and to which it will attach. Beneath a specific depth, the layer is closed to penetration by fluids and collagen and to tissue in growth by an adhesive that bonds the transition layer to the boundary layer. This adhesive penetrates into the transition layer toward its exposed surface far enough to seal its "cells" beneath that specific depth, but not so far as to seal the outer "cells". Thus, the tissue-receptive region permits controlled tissue in growth to the precise depth extent needed for acceptance and fixation of the prosthesis, but inhibits penetration and in growth in excess of that amount, thereby avoiding the firm encapsulation so frequently experienced in the prior art. In fact, the result appears to be the formation of a multitude of individual encapsulations around the various rough structures, but these encapsulations do not join up to form a grossly firm or hard encapsulation.

According to an optional feature of this invention, when this invention is incorporated into a mammary prosthesis, the bulk medium is made of a gel which is substantially self-shape retaining at body temperatures. While it is supple and palpable, it has sufficient memory to return to its normal shape. It does not slump appreciably at body temperatures. The boundary layer is a coating of a resilient sealant which itself elastically and flexibly adapts to changes in the shape of gel core such as are caused by palpation. No claim of originality is made to this form of core per se.

Optimally, the boundary layer could be a pre-formed envelope of more substantial thickness in which the gel is poured and cured. This envelope itself may provide some shape retention properties, and it might retain liquids instead of a gel. Again, no claim of originality is made to this form of core per se.

Another optimal feature of the invention is to provide as the core a hard case, and apply the transition layer to it as described. This embodiment is claimed to be original.

According to yet another preferred but optional feature of the invention, the tissue-receptive layer is an open-cell microfiber foam, laser-cut to a precise and uniform thickness so as to form those micro-fiber-like structures preferably without loose fragments, and so the depth of penetration can be precisely determined and controlled. There are approximately seven linear cross-linked fibers of less than about 0.01 mm thickness each per mm along the surface, totally free of friable pieces in the preferred material.

According to another form of the invention, the core may be left unsealed against the egress of certain molecular sizes so that medicines may exude from the implant.

The above and other features of this invention will be fully understood from the following detailed description and the accompanying drawings in which:

BRIEF DESCRIPTION OF THE DRAWINGS

FIG. 1 is a side view of a mammary prosthesis incorporating the presently preferred embodiment of the invention;

FIG. 2 is a top view of FIG. 1;

FIGS. 3-7 show successive steps in the manufacture of the prosthesis of FIG. 1;

FIG. 8 is a bottom view of FIG. 1;

FIG. 9 is a schematic showing of one form of optional shape support;

FIGS. 10 and 11 are respectively side fragmentary top views of another optional internal shape support;

DETAILED DESCRIPTION OF THE INVENTION

Figure 12:
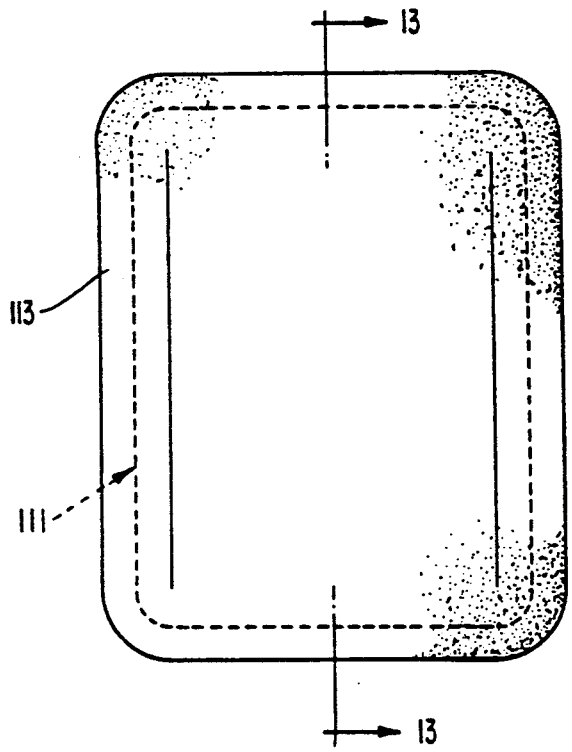
FIG. 12 is a plan view of pacemaker incorporating the invention.

FIG. 1 shows the general contours of a mammary prosthesis 20 which incorporates the invention. This prosthesis is used for augmentation. Such prostheses may have numerous shapes and purposes. This invention is not limited to the shapes shown or to mammary applications. It is of general applicability.

A very common shape which is related to the external contour of the breast which can be for tissue replacement or augmentation is shown in FIG. 9. Other shapes can be made for other types of replacements, for example, in the neck or shoulder. For such other uses, the shape of the prosthesis will be made to conform to and fill the respective region of the body. The illustrated shape in FIG. 1 is a useful one for breast augmentation and is a useful example for teaching how to manufacture any suitably shaped prosthesis according to the invention. Other types can be similarly manufactured and appropriately shaped for the intended use.

With respect to the cross section shown in FIG. 7, wherein the various layers are shown disproportionately thick for purposes of illustration, the prosthesis 20 is shown having a core comprising a bulk medium 21 with an outer boundary layer 22. Layer 22 is a sealant contiguous to and adherent to the outer surface of the gel itself. Medium 21 and layer 22 comprise a "core" Layer 22 seals the bulk medium from fluid migration into it, and is intended to make as good a seal to prevent outward bulk material migration as possible. Layer 22 in the example is a formed-in-place layer, applied to a gelled core. Alternatively, it may instead be a preformed envelope of similar material, into which core material is placed. This core material may remain fluid, or may be cured to a self-shape retaining condition as preferred. This layer is considered to be a portion of the core.

An adhesive layer 23 is applied to the boundary layer, and a transition layer 24 is adhesively bonded to the sealant layer by layer 23. The transition layer is formed from two sheets 25 and 26, each laid upon a respective side of the core. The edges of the sheets are heat sealed together to form a continuous, thin and very flexible feathered edge 27, all as will be more fully described below.

The features and functions of the various portions of prosthesis 20 will now be described, principally in connection with its method of manufacture.

In FIG. 3, a mold 30 is shown having a cavity 31 formed between two mold parts 32 and 33. A suitable vent 34 or vents will be provided for supply and venting in accordance with conventional molding practice.

The materials which form the gel will be poured through the vent or other supply passage and the gel will be cured while in the mold, the cavity having been formed to the ultimately desired shape. The composition of the gel and the chemical methods for forming it will be described later.

After the gel has been fully cured in the mold (the mold usually being heated to assist in the gelation process), the gel will itself constitute a self-shape retaining body - a bulk medium. It is, however, sticky and difficult to handle. Furthermore, despite all efforts to remove unreacted materials, there sometimes will be some present. For these reasons, it is good practice and efficacious to encapsulate the gel core in an outer boundary layer, preferably a thin, flexible and elastic sealant layer.

The outer boundary layer should be resilient and deformable so that its shape can readily change to conform to changes in the shape of the prosthesis caused by such actions as squeezing, and impermeate to the gel and its components unless for some reason permeation is desired. It is a sealant, and will be adherent to, contiguous with, and continuous with the outer surface of the bulk medium. The combination of gel and sealant is an example of a suitable core for a prosthesis. As will later be evident, this is merely one example of a useful core.

The boundary layer is applied, preferably while the gel core is still in its mold, by brush coating or knife coating the gel core with one part of the mold removed, then curing it, then turning the core over into the other mold part and coating and curing the other surface after removing the other mold part. This is a painstaking task, because the boundary layer when applied in this way is not intended to be more than approximately 0.002 inch thick, and complete coating of the surface is desired without excessive build up of material anywhere. When the boundary layer is cured, the core can be handled as a unit. It is only slightly tacky. The gel will not appreciably penetrate the boundary layer.

Transition layer 24, comprised of sheets 25 and 26, is laid upon the outer boundary for fixation and in growth of tissue. While other materials can be used instead, it has been found that very beneficial results are obtained when the transition layer is made from an open cell foam.

With this invention, encapsulation with gross properties approaching those of the surrounding tissues are obtained. The foam is made from any material which is compatible with body tissues and fluids. At the present time polyurethane foam is the best substance. However, as they become available, foams of teflon, polypropylene and dacron will also be suitable. The foam is formed as a block, and sheets are cut from it to form a surface of micro-fiber structures, without friable particles. The cell size and population are such that a laser cut produces a surface with about seven linear cross-linked fibers of less than 0.01 mm thickness each per mm along the surface, free of friable pieces. In order to provide uniform tissue retention properties and tissue penetration properties over the entire surface of the prosthesis, a very uniform thickness of sheets 25 and 26 is necessary. The most careful knife cut can provide such uniformity, but only with difficulty. It is much simpler, and far more accurate, to cut these sheets from a block of foam using a laser beam.

The foam is high density, so that the cells are quite small. The sheet thickness is about 1.0 mm. The uniformity of thickness is of nearly as great importance as the actual thickness. Sheets this thin of such material are readily penetrated by fluids. The purpose of these sheets is not to resist penetration by a fluid, but at one side to provide an innermost surface to be bonded to the boundary layer, and an outermost roughened surface with a large number of micro thin fiber-like strands around which tissue can grow. Furthermore, it is desired that the depth of this penetration by tissues and fluids be limited. In this invention these results are obtained by laser cutting of the sheets, which enables the thickness to be very closely controlled, and by penetration of the adhesive into the layer to a specific depth, so as to close the foam to further penetration by tissues and fluids.

The depth of penetration is best controlled by choosing the appropriate viscosity of the adhesive, and the amount of liquid adhesive applied. Too much adhesive will soak through, and too little will either not make the bond to the boundary surface, or will not penetrate far enough. Uniform and accurate application of the adhesive is an acquired skill, but it is one that can be learned.

In the next step of manufacture as shown in FIG. 5, the layer of liquid adhesive 23 is applied to the surface of the sealant layer, usually by a brush or by a knife or trowel.

Blotting the surface to remove excess sealant is also a useful technique. Then one of the sheets is laid carefully over the surface of adhesive, without minimum stretching or bunching. The prosthesis is turned over and the other sheet is applied in the same way. The sheets are carefully smoothed out, care being taken not to thin them out too much by excessive (or any) stretching. The adhesive, being liquid until it cures, penetrates into the foam. The viscosity and amount of the adhesive are carefully regulated such that it penetrates only as far as desired, so as to leave a correct volume of unoclouded micro-fiber structures and open cells, while sealing the innermost cells and adhering the transition layer to the core.

The edges 35 of the sheets are brought together as shown in FIGS. 6 and 7, and a heat sealing iron is brought down against them immediately adjacent to the core. This melts the polyurethane which projects beyond the core of the prosthesis and fuses the layers together to form a flexible and thin feathered edge, which neatly finishes the edge of the prosthesis without creating a hard, palpable structure. A hard edge structure has been a known disadvantage of some prior art prostheses. This edge can be used as additional attachment and orientation means.

FIG. 9 shows an optional construction of a prosthesis 40 in which three webs 41, 42, 43 are Joined together at a trihedral edge 44, and are embedded in a gel structure 45 which can then receive boundary layer 22 as before to form a core. Prosthesis 40 may be finished with an adhesive layer and transition layer (not shown) as in FIG. 1. This is a prosthesis of the same type, but with internal reinforcement and a different shape.

Other means can also be provided to improve the shape retention of the device and one such means is shown in FIGS. 10 and 11 where a reinforcement plate 50 is shown with a base 51 which can fit inside the bulk medium near one of its sides, and a honeycomb structure 52 with open ended cavities 53 rising from it. Gel poured into these cavities and around the structure will have a basic structure less subject to slump and deformation. Such internal reinforcements as shown in FIGS. 9, 10, and 11 are optional and usually will not be required or used.

Any type of core can be finished with the transition layer as described. For example, a silicone sac or envelope adapted to hold a liquid can have the same adhesive layer and transition layer to form attachment means for the prosthesis, thus giving it additional and beneficial properties. In such event, the envelope would be pre-formed and then filled with fluid which may either remain fluid, or be cured to be self-shape retaining.

Figure 14:
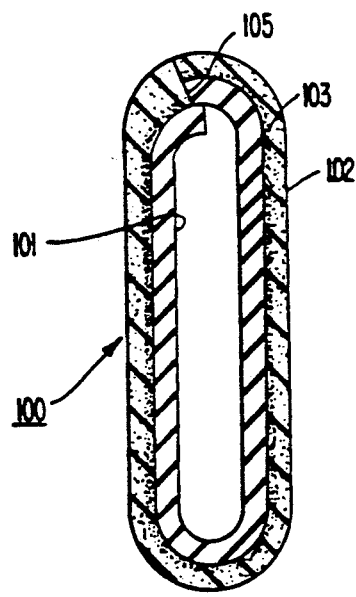
FIG. 14 is a cross-section of another embodiment of the invention.

As an extension of this concept, there is shown in FIG. 14 a pouch or sac 100 shown which has a pouch-like fluid-impermeable skin or envelope 101. A transition layer 102 identical to the previously described transition layer is attached to it including the adhesive material 103 partially migrated into it over substantially its entire surface. Any desired device, such as a pace-maker, can be inserted into the pouch through opening 105, and the opening will then be closed. All advantages of this invention are then attained.

As to the materials of construction, the bulk medium is a gel preferably made of medical grade dimethyl polysiloxane of the type obtainable from Dow Corning Corporation. It is a two component system, and the properties of the gel will be determined by the proportion of the cross-linker in the two component mixture. This material is usually mixed in a batch to make a number of gel structures in a plurality of molds at the same time The proportions are selected such that a two inch diameter, one half inch thick, disk of the cured material when bent ninety degrees will be slightly wrinkled all over its inside surface. Such test disks can readily be made and cured on an accelerated basis to make this test in order to adjust the relative proportions of the two components. When in the mold (and the mold may be an epoxy mold instead of metal if desired) curing will usually take about sixteen hours at approximately 150 degrees F.

The boundary layer 22 is also made of medical grade dimethyl polysiloxane from Dow Corning Corporation and is also heat cured. Its thickness is preferably about 0.002 inches. When applied wet and cured. A pre-formed envelope will usually have a thickness between about 0.008 and 0.015 inches. The adhesive layer 23 is a room-temperature vulcanizing medical grade dimethyl polysiloxane obtainable from Dow Corning Corporation and also is applied as a very thin layer so as to penetrate only a small distance into the transition tissue layer 24, usually to about one half of the thickness. Certainly too little is provided for the adhesive to soak all the way through the foam. The outer foam surface must be adhesive-free to such an exists that an adequate depth of exposed fibers and unsealed cells exist for retention and penetration and continuity of cells and fluids. Uniformity of penetration over the entire surface is an objective.

The transition layer is preferably approximately one millimeter thick and is made of high density polyurethane, open-cell material with cell size and population as specified elsewhere to give correct properties. Because the outermost surface of the transition layer is made by a straight cut across a block, the density of fibers is a function of the foam cell population and size. The fibers are, of course, the remnants of the foam cell walls, and are of random shape. This provides a desirable surface "roughness" in the sense of inconsistencies, but within acceptable size range. Just beneath this group of fibers there is a region of complete open cells. These permit cell and fluid penetration. However, the depth of this region is limited by the incursion of the adhesive, which fills the cells on the bottom side to the appropriate depth.

Of course, the transition layer could be provided as a pair of joined-together layers, for example, with an outer surface adapted for tissue in growth and fluid penetration, and another foam layer attached to it and to the boundary layer for structural reinforcement of the outer layer and attachment to the core, but this would be a difficult structure to make, especially in contrast to the easily manufactured layer described above. The inner layer would then be closed foam, or even an impermeable material.

As should be evident from the foregoing, a core having a gel center is merely one embodiment. The surface treatment of the prosthesis can be applied to any type of core, and its utility is not limited to usage with a gel-filled or shape-retaining core. The utility and application of all types of cores can be remarkably improved - even the liquid-filled envelope type.

The total thickness of the outer layer is not of importance except to the extent that it might adversely affect the gross properties of the prosthesis. What is important is the quality and depth of the surface which permits penetration and in growth, i.e., the region of open cells and fibers. This depth should be just sufficient to permit fixation, and should be insufficient to provide such depth for collagen and tissue incursion that a firm capsule can be contributed to.

It will be noted in FIGS. 1 through 8 that the prosthesis has a relatively rounded side, and a frusto-conical side. In plan it is circular. This is a useful shape for augmentation. The frusto-conical side faces the rib cage. When the breast is brought down against it, the frusto-conical shape gives some lateral restraint, so the prosthesis does not tend to flatten and roll as a pillow. This is an example of the wide range of shapes and functions which are attainable with this invention.

Figure 13:
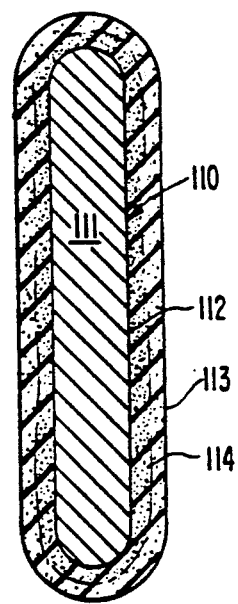
FIG. 13 is a cross-section taken at line 13—13 in FIG. 12.

FIGS. 12 and 13 show a core 110 comprising an article 111 to be implanted, such as a pacemaker. Instead of being placed in a pouch as in FIG. 14, its own surface 112 is used to support the transition layer. The transition layer 113 is adhered to the article by adhesive 114 which penetrates part way into the transition layer. It is in all ways identical to the transition layers described above. A metal case requires no sealing.

While the cores described this far have been described as sealed, it will be recognized by persons skilled in the art that silicone articles will over the years exude some of their material. A sufficient sealant thickness is provided to at least repress this effect, and this is defined as "sealed". Of equal concern is the tendency of some lower molecular weight materials to migrate into the core. Again the integrity and thickness of the sealant are intended to be such as to repress this tendency.

In fact, the use of a pre-formed envelope will often be preferred to the use of a sealant which is applied to the bulk material. This is because the envelope can be tested for flaws and leaks, while the applied sealant layer cannot be tested.

Figure 15:
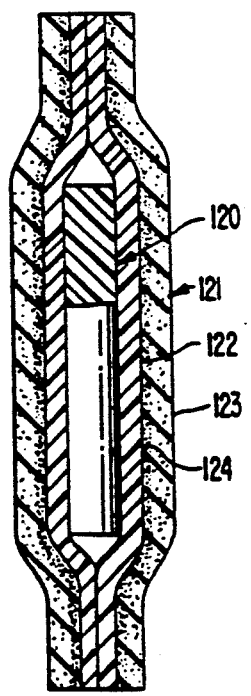
FIG. 15 is a cross-section of still another embodiment of the invention.

FIG. 15 shows an extension of the inventive concept. A rod 120 of a material that is infused with a medication is intended to be implanted in the body, and remain there for a considerable period of time. There are presently proposed such rods with a contraceptive pharmaceutical which are expected to remain implanted for up to five years. During this time a steady migration of the pharmaceutical is intended, and a encapsulation could frustrate this objective. In this situation, the invention provides for fixation and closure of the transition layer to incursion of tissue and fluids below a give depth. But the sealant is selected so as to accommodate migration of the pharmaceutical through it.

In FIG. 15, rod 120 is placed within a sleeve 121. The sleeve is crimped or otherwise sealed at both ends. It has a boundary layer 122 and a transition layer 123. The transition layer is adhered to the boundary layer by adhesive 124 as described in the other embodiments.

Thus, this invention provides a tissue-compatible interface for many types of implants and prostheses. It can be applied directly to the core article itself, as in FIGS. 1—13, or can be applied to a cover as in FIG. 14. For definition purposes, the "cover" can be considered as a core or as part of a core.

Test implants in animals have shown that prostheses with a transition surface as described are well-received. There is no tendency to harden or to become firmly encapsulated or distorted, and the properties are remarkably consistent all over the surface.

This invention is not to be limited by the embodiments shown in the drawings and described in the descriptions, which are given by way of example and not of limitation, but only in accordance with the scope of the appended claims.

I claim:

1. A method of forming a surgical implant which resets the formation of firm spherical encapsulation comprising steps of:
   providing a silicone substrate implant,
   providing first and second sheets of open-cell foam;
   physically bonding said first and second sheets, with an adhesive layer, to adjacent portions of the outer surface of said silicone substrate implant, and
   thereafter, heat sealing adjacent edges of said first and second sheets together,
   said bonding including said adhesive layer penetrating into said first and second sheets so that uncoated and unclouded cells and fibers remain at the outer surfaces of said sheets to a depth sufficient for surrounding tissue to become structurally congruent over the surface which is contiguous to tissue and to a depth insufficient to permit invasive in growth which would result in the formation of a grossly palpable, rigid, and fibrous encapsulation of the implant.

2. The method of claim 1 including,
   said heat sealing including thereby forming a continuous, thin, flexible feathered edge at the junction of said fist and second sheets.

3. The method of claim 1 including,
   said first and second sheets covering the entire outer surface of said implant with a single sheet layer.

4. The method of claim 1 including,
   before said bonding, laser cutting said fist and second sheets from a block of foam.

5. The method of claim 1 including,
   said foam being polyurethane foam and said adhesive layer comprising silicone adhesive.

6. The method of claim 1 including,
   said heat sealing including applying a heat sealing iron to the edges of said first and second sheets.

7. The method of claim 1 including,
   said bonding including applying said first sheet to one portion of said implant and said second sheet to an opposite portion of said implant so that the juncture of said first and second sheets encircles said implant and said implant thereby is covered by a single sheet layer.

8. The method of claim 1 including,
   before said bonding, cutting said first sheet so as to open some of the cells on its inner and outer surfaces, and at least on said outer surface thereby forming a substantial number of cellwall fragments to form fibers for tissue contiguity.

9. The method of claim 1 including,
   before said bonding, forming said implant of a gel-sealant combination.

10. The method of claim 1 including,
    said implant having a the generally flat portion, a rounded portion and a radius where said flat portion stops and said rounded portion starts, and said heat sealing being generally at said radius.

11. The method of claim 1 including,
    forming said sheets of a single chain, co-polymer polyurethane.

12. The method of claim 11 including,
    forming said implant of a gelled medical grade dimethyl polysiloxane.

13. The method of claim 1 including,
    said bonding step including applying the adhesive layer to said outer surface f said silicone substrate implant and then laying said first sheet on said adhesive layer while the adhesive is still liquid.

14. The method of claim 13 including,
said applying including brush coating said adhesive layer to said outer surface.

15. The method of claim 13 including,
said applying including knife coasting said adhesive layer to said outer surface.

16. The method of claim 13 including,
after said laying, smoothing said fist sheet on said adhesive layer.

17. The method of claim 1 including,
before said bonding, forming said silicone substrate implant in a mold comprising first and second mold parts.

18. The method of claim 17 including,
at least a portion of said bonding step being done with said silicone substrate implant positioned in said first mold part.

19. A method of forming a surgical implant which resists the formation of firm spherical encapsulation comprising the steps of:
providing a self-shape retaining substrate implant,
providing first and second sheets of open-cell foam;
physically bonding said first and second sheets, with an adhesive layer, to adjacent portions of the outer surface of said substrate implant, and
thereafter, heat sealing adjacent edges f said first and second sheets together,
said bonding including said adhesive layer not penetrating only pat-way into said first and second sheets so that uncoated and unclouded cells and fibers remain at the other surfaces of said sheets to a depth sufficient for surrounding tissue to become structurally congruent over the surface which is continuous to tissue and to a depth to inhibit the formation of a grossly palpable, rigid, and fibrous encapsulation of the implant.

* * * * *